United States Patent [19]

Gretzinger et al.

[11] Patent Number: 4,852,414
[45] Date of Patent: Aug. 1, 1989

[54] DEVICE FOR INSERTING AND REMOVING THE SAMPLE IN AN ANALYSIS OVEN

[75] Inventors: Klaus Gretzinger, Moembris; Erich Wombacher, Bessenbach, both of Fed. Rep. of Germany

[73] Assignee: Leybold Aktiengesellschaft, Hanau

[21] Appl. No.: 157,329

[22] Filed: Feb. 17, 1988

[30] Foreign Application Priority Data

Jan. 7, 1988 [DE] Fed. Rep. of Germany ....... 3800189

[51] Int. Cl.$^4$ .............................................. G01N 1/28
[52] U.S. Cl. .................................... 73/864.85; 422/78
[58] Field of Search ........................ 73/863.11, 864.85; 422/78

[56] References Cited

U.S. PATENT DOCUMENTS

| 2,610,107 | 9/1952 | Dreher | 422/78 |
| 4,055,259 | 10/1977 | Sibraua | 422/78 X |
| 4,634,865 | 1/1987 | Conway | 73/864.85 X |
| 4,702,114 | 10/1987 | Cabannes | 73/863.11 X |

Primary Examiner—Tom Noland
Attorney, Agent, or Firm—Felfe & Lynch

[57] ABSTRACT

In a device for inserting and removing the sample from an analysis oven, which has a transport rod (9) carried horizontally and for longitudinal displacement in a guiding member or carrier tube (3) affixed to the apparatus, and a sample holder (33) disposed on one end of the transport rod (9), plus a handle part (36) joined to the transport rod (9), the transport rod (9) is in the form of a shaped rod with a plurality of flats (10 to 13) extending along the rod (9), several roller pairs (21, 22 and 26, 27) mounted in the carrier tube (3) and partially spring loaded and movable transversely of the transport rod (9) lying against these flats (11, 12) or on the rounded portions (46), and holding and guiding the transport rod (9) in a longitudinal movement, on the one hand, and on the other hand permitting a rotatory movement about its longitudinal axis, so that the sample can be dumped from the transport rod (9) when the analysis is completed.

12 Claims, 1 Drawing Sheet

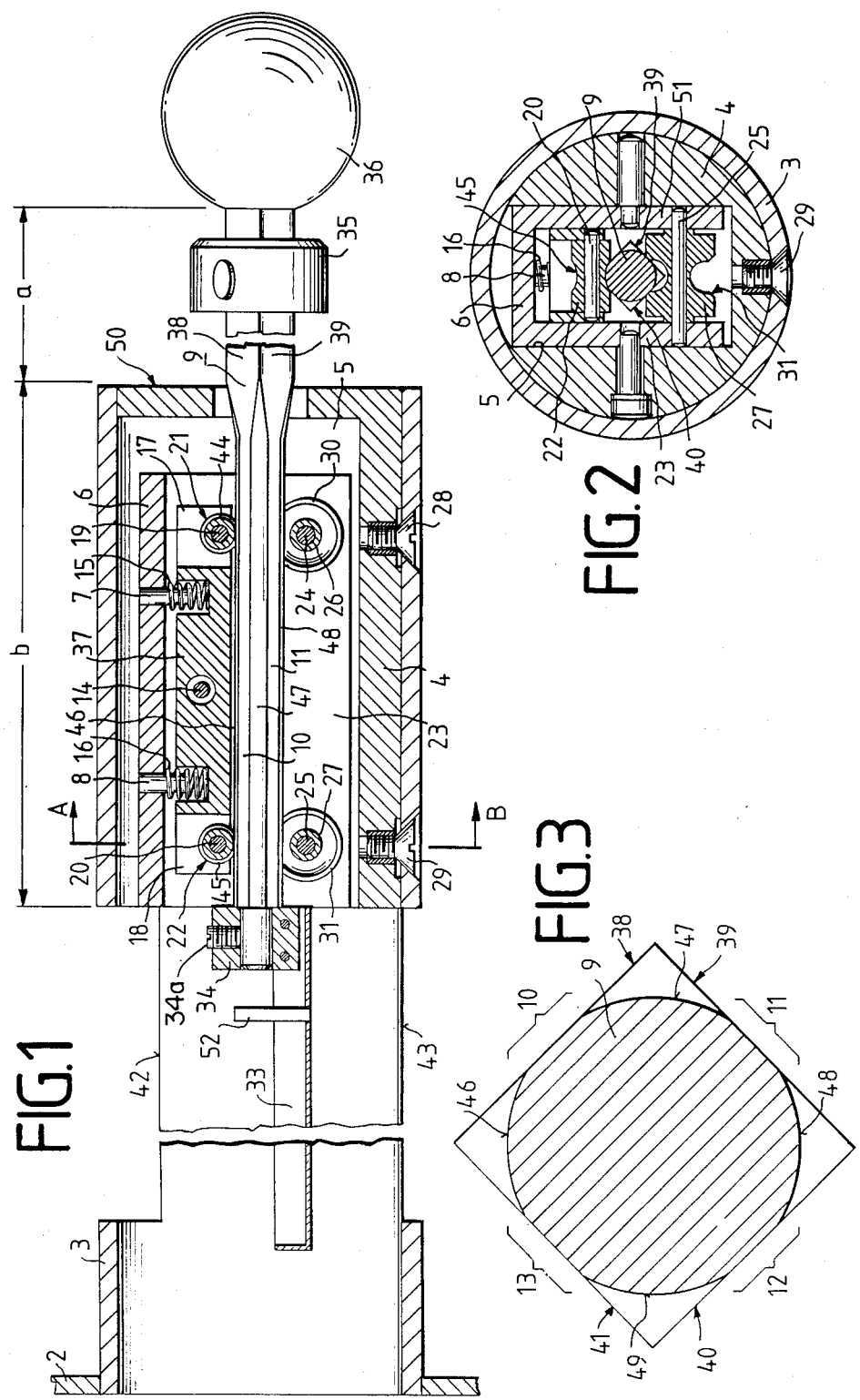

DEVICE FOR INSERTING AND REMOVING THE SAMPLE IN AN ANALYSIS OVEN

BACKGROUND OF THE INVENTION

The invention relates to a device for inserting and removing the sample in an analysis oven. The device has a transport rod mounted horizontally and for longitudinal displacement in a guide or carrier tube affixed to the apparatus, a sample holder disposed at one end of the transport rod, and a handle joined to the transport rod or a motor drive operatively connected to the handle.

An apparatus of the kind in question is known in which the transport rod is provided at its oven end with a hook on which a simple crucible is placed or hooked, which can be then inserted into the tubular oven of the analyzer. After the measurement has been performed the sample crucible can be removed again from the tubular oven and returned to the starting position by means of the transport rod. The sample crucible can then be removed from the hook, but experience has shown that this is time-consuming, since tongs or gloves must be used for this purpose on account of the high temperature of the sample crucible.

It is the object of the present invention to improve the previously known device such that the insertion and removal of the sample and sample crucible can be performed very conveniently and, in particular, with great speed. The device is to assure that the sample and sample crucible cannot come loose from the transport rod when the latter is in its forward, i.e., inserted, position. Lastly, the device is to assure that a crucible that breaks during the analysis will remain entirely or else partially in the oven when the transport rod is returned to its starting position.

SUMMARY OF THE INVENTION

This object is achieved according to the invention by the fact that the transport rod is especially shaped in cross section with one or more flats extending along the transport rod, while several slides or pairs of rollers mounted in the carrier tube or on a guide disposed in the latter, some of them spring loaded, and movable transversely of the transport rod, engage these flats or the rounded portions and hold and guide the transport rod in a longitudinal movement and on the other hand permit it to perform a rotating movement about its longitudinal axis.

Preferably, the transport rod is given a square cross section in a first portion and has in the second portion a substantially circular cross section which is provided with a total of four flats disposed parallel to one another in pairs, which extend in the same planes with the four surfaces forming the first section of the transport rod, the rollers engaging the four flats of the second action or the two corresponding surfaces of the first section, depending on the position of the transport rod with respect to the carrier tube.

The fact that the first section of the transport rod is of square cross section assures that the transport rod will not be rotatable about its longitudinal axis as long as this first section is in the area of the rollers.

Advantageously the rollers of the one pair of rollers are provided with circumferential grooves whose flanks facing the transport rod lie against the flats of the transport rod when the latter is in its starting position, the rollers of the other pair of rollers being provided with comparatively narrow circumferential grooves whose flanks engage a rounded portion of the transport rod between two flats.

It is desirable for the one pair of rollers to be mounted on a slide which is supported by compression springs on the carrier tube or on a guiding body held on the carrier tube, and which permits a movement of the pair of rollers across the longitudinal axis of the transport rod.

Inasmuch as at least one pair of rollers is mounted for transverse displacement with respect to the transport tube, it is possible to rotate the transport rod about its longitudinal axis when this second portion is situated in the range of the roller pairs. In case of a rotatory movement the two adjacent flats on the transport rod slip out of the circumferential grooves of the one roller pairs, so that then another pair of flats can slide into these grooves.

In an alternative embodiment, the rollers of the one roller pair are mounted on spring-loaded guides which in turn are held and guided for movement with respect to the carrier tube and which permit a movement of the individual rollers in a direction across the longitudinal axis of the transport rod.

To permit a precise positioning of the sample in the tubular oven, the transport rod is provided in its first portion with an abutment which limits the longitudinal movement of the transport rod in the actuating direction and for that purpose abuts against the end of the carrier tube or of the insert for the guide body.

It is desirable for a dish-like sample carrier to be fastened to the end of the transport rod at the analysis oven, the carrier tube being provided with openings or notches in the area between the guide body on the one hand and the holding plate or front plate of the analysis oven to permit the sample to be placed on the sample carrier and permit the sample to be dumped out.

BRIEF DESCRIPTION OF THE DRAWINGS

The invention admits of a great variety of embodiments; one of them is represented diagrammatically in the appended drawings, wherein:

FIG. 1 is a longitudinal section through a device for charging a tubular oven of an automatic analyzer.

FIG. 2 is a cross section of the insert taken along lines A–B of FIG. 1.

FIG. 3 is an enlarged cross section taken through the transport rod.

DESCRIPTION OF THE PREFERRED EMBODIMENT

The device consists essentially of a horizontally extending carrier tube 3 disposed fixedly on a vertical front plate 2 of the tubular oven, an insert 4 mounted in the carrier tube 3 and fastened with screws 28 and 29, an inverted U-shaped guide 6 inserted into a channel 5 of the insert 4 and having a plurality of guide pins 7 and 8 extending across the longitudinal axis of the carrier tube 3, a transport rod 9 displaceable lengthwise of the carrier tube 3 and having four flats 10, 11, 12 and 13 uniformly distributed on its circumference and extending longitudinally, a slide 37 held and guided by the guide pins 7 and 8, a cross pin 14 limiting the movement of the slide 37, two compression springs 15 and 16 thrusting between the slide 37 and the guide 6, two rollers 21 and 22 journaled in cutouts 17 and 18 on pins 19 and 20 held by the slide 37, two supporting rollers 26 and 27 which are journaled in the side parts 23 and 51 of the guide 6 on the shafts 24 and 25, and whose circumferential grooves 30 and 31 lie against the parallel flats 11 and 12 of the transport rod 9 and a dish-like sample holder 33 affixed to the transport rod 9 and having the bushing 34 and pin 34a.

Between the rollers 21 and 22, which are preferably made of a bearing material, the transport rod 9 can be displaced linearly and coaxially with the carrier tube 3. The transport rod 9 is shaped in the area of the section b such that a 360° rotation about its longitudinal axis is possible between the rollers 21 and 22 and the supporting rollers 26 and 27.

The transport rod 9 is provided at the end remote from the sample holder 33, outside of the carrier tube 3, with an axially adjustable stop 35 and an operating handle 36. Within the carrier tube 3 the sample holder 33 is releasably attached to the transport rod 9 by the bushing 34, so that the replacement of a damaged or contaminated sample holder 33 can be performed easily.

For the insertion and removal of a sample the carrier tube 3 has a top opening 42 and a bottom opening 43.

For the analysis a sample can be placed directly on the sample holder 33, in a sample vessel designed for the sample holder 33 and the oven temperature (vitreous fused silica, ceramic, metal etc.), or it can be put through the upper opening 42 of the carrier tube 3 into the sample holder 33. By axial displacement of the transport rod 9 the sample to be analyzed can be put into the tubular oven, the stop 35 assuring any desired repeatable positioning of the samples in the tubular oven. After completion of the analysis, by pulling back and then turning the transport rod 9 by about 180° the sample or the sample vessel with sample can be dropped from the sample holder 33 through the bottom opening 43 into a container not shown in detail. The guidance of the transport rod 9 during the rotatory movement is stabilized by the resiliently mounted slide 37. By turning the transport rod 9 back 180° or by turning it further, the sample holder 33 is put back into its starting position for taking a sample.

We claim:

1. Apparatus for the insertion and removal of a sample in an analysis oven, comprising:
    a horizontal carrier tube affixed to the apparatus;
    a transport rod mounted horizontally and for longitudinal displacement in the carrier tube along a longitudinal axis thereof;
    a sample carrier disposed at one end of the transport rod;
    means for driving the transport rod in operative connection with the transport rod, the transport rod comprising a shaped rod having rounded portions and having at least one flat portion extending along the transport rod; and
    a slide which is mounted in the carrier tube and which is spring loaded and movable transversely of the transport rod and which has portions which lie on at least one of the group consisting of the flat and the rounded portions and which slide portions hold and guide the transport rod in a longitudinal movement on the one hand, and on the other hand permit a rotary movement about its longitudinal axis.

2. Device according to claim 1, which includes a dishlike sample holder forming said sample carrier held and guided at a distance from the carrier tube, so that contact of a sample crucible carried by the sample holder with the carrier tube is prevented.

3. Apparatus for the insertion and removal of a sample in an analysis oven, comprising:
    a horizontal carrier tube affixed to the apparatus;
    a transport rod mounted horizontally and for longitudinal displacement in the carrier tube along a longitudinal axis thereof;
    a sample carrier disposed at one end of the transport rod;
    means for driving the transport rod in operative connection with the transport rod, the transport rod comprising a shaped rod having rounded portions and having at least one flat portion extending along the transport rod;
    a guide disposed in the carrier tube; and
    a slide which is mounted on the guide disposed in the carrier tube and which is spring loaded and movable transversely of the transport rod and which has portions which lie on at least one of the group consisting of the flat and the rounded portions and which guide portions hold and guide the transport rod in a longitudinal movement on the one hand, and on the other hand permit a rotary movement about its longitudinal axis.

4. Device according to claim 3, which includes an adjustable stop on the transport rod, the adjustable stop limiting the longitudinal movement of the transport rod in the direction of actuation and for that purpose abutting against an end of the guide.

5. Device according to claim 3, which includes, on an end of the transport rod facing the analysis oven, a dish-like sample holder forming said sample carrier, the carrier tube being provided with openings in an area between the guide on the one hand and the analysis oven on the other hand, which permits placement of a sample on the sample holder and the dumping out of the sample.

6. Apparatus for the insertion and removal of a sample in an analysis oven, comprising:
    a horizontal carrier tube affixed to the apparatus;
    a transport rod mounted horizontally and for longitudinal displacement in the carrier tube along a longitudinal axis thereof;
    a sample carrier disposed at one end of the transport rod;
    means for driving the transport rod in operative connection with the transport rod, the transport rod comprising a shaped rod having rounded portions and having at least one flat portion extending along the transport rod; and
    a plurality of roller pairs which are mounted in the carrier tube and which are at least partially spring loaded and movable transversely of the transport rod and which lie on at least one of the group consisting of the flat and the rounded portions and which roller pairs hold and guide the transport rod in a longitudinal movement on the one hand, and on the other hand permit a rotary movement about its longitudinal axis.

7. Device according to claim 6, in which the transport rod is profiled in a first section as a square rod with four surfaces and which transport rod in a second section has a substantially circular profile which is provided with a total of four, pair-wise parallel flat portions which extend in the same planes with the four surfaces of the first section of the transport rod, while the roller pairs lie against at least one of the group consisting of two flat portions of the second section and the two corresponding surfaces of the first section, according to the position of the transport rod in relation to the carrier tube.

8. Device according to claim 6, in which a roller of one roller pair has a circumferential groove having flanks facing the transport rod and on whose flanks the flat portions of the transport rod lie when the latter is in a starting position, another roller of the one roller pair being provided with a comparatively narrow circumferential groove which lies against a rounded portion of the transport rod.

9. Device according to claim 6, which includes a first roller of the roller pairs and having a circumferential groove having a semicircular cross-sectional profile, the radius of this cross-sectional profile corresponding to the radius of the rounded portions of the cross-sectional profile in the transport rod, and which includes a second roller of the roller pairs and having a circumferential groove having an approximately V-shaped configuration, so that, with the transport rod in a starting position, two adjacent flat portions lie against the last-mentioned groove.

10. Apparatus for the insertion and removal of a sample in an analysis oven, comprising:
 a horizontal carrier tube affixed to the apparatus;
 a transport rod mounted horizontally and for longitudinal displacement in the carrier tube along a longitudinal axis thereof;
 a sample carrier disposed at one end of the transport rod;
 means for driving the transport rod in operative connection with the transport rod, the transport rod comprising a shaped rod having rounded portions and having at least one flat portion extending along the transport rod;
 a guide disposed in the carrier tube; and
 a plurality of roller pairs which are mounted on the guide and which are at least partially spring loaded and movable transversely of the transport rod and which lie on at least one of the group consisting of the flat and the rounded portions and which roller pairs hold and guide the transport rod in a longitudinal movement on the one hand, and on the other hand permit a rotary movement about its longitudinal axis.

11. Device according to claim 10, which includes compression springs and in which one roller pair is mounted on a slide which is supported by the compression springs on the guide held in the carrier tube and which permits a movement of at least the one roller pair transversely of the longitudinal axis of the transport rod.

12. Device according to claim 10, in which the rollers of one roller pair are mounted and spring-loaded with respect to the guide which in turn is held and guided for movement with respect to the carrier tube and which permits a movement of individual rollers in a direction across the longitudinal axis of the transport rod.

* * * * *